United States Patent [19]

Dickinson et al.

[11] Patent Number: 4,489,779
[45] Date of Patent: Dec. 25, 1984

[54] FLUID SAMPLING APPARATUS

[75] Inventors: William D. Dickinson, Ypsilanti; David Mioduszewski; Frederick E. Bernardin, Jr., both of Ann Arbor, all of Mich.

[73] Assignee: Quantitative Environmental Decisions Corporation, Ann Arbor, Mich.

[21] Appl. No.: 470,305

[22] Filed: Feb. 28, 1983

[51] Int. Cl.³ ............................................. E21B 49/08
[52] U.S. Cl. ....................................... 166/64; 73/302; 73/804.34; 417/394; 166/68; 166/105
[58] Field of Search ............... 166/66, 105, 680, 113, 166/64; 73/302, 864.34, 864.35; 417/394, 478

[56] References Cited

U.S. PATENT DOCUMENTS

| | | |
|---|---|---|
| 2,606,500 | 8/1952 | Schmidt . |
| 2,931,309 | 4/1960 | Bower . |
| 3,039,309 | 6/1962 | Vesper et al. ............... 73/864.34 |
| 3,048,121 | 8/1962 | Sheesley . |
| 3,074,351 | 1/1963 | Foster . |
| 3,154,021 | 10/1964 | Vick, Jr. . |
| 3,173,372 | 3/1965 | Baldwin . |
| 3,175,498 | 3/1965 | Rohrer . |
| 3,194,170 | 7/1965 | Ulbing . |
| 3,298,320 | 1/1967 | Latham, Jr. . |
| 3,393,740 | 7/1968 | Seese et al. ............... 166/68 |
| 3,431,347 | 6/1969 | Chinura ................... 417/394 |
| 3,677,667 | 7/1972 | Morrison . |
| 3,724,973 | 4/1973 | Shill . |
| 3,816,032 | 6/1974 | Flynn et al. . |
| 3,880,011 | 4/1975 | Johnson ................... 73/864.5 |
| 3,949,753 | 4/1976 | Dockhorn . |
| 3,983,857 | 10/1976 | O'Connor . |
| 3,987,775 | 10/1976 | O'Connor . |
| 4,010,642 | 3/1977 | McArthur .................. 73/302 |
| 4,020,978 | 5/1977 | Szczepanski . |
| 4,030,640 | 6/1977 | Citrin et al. . |
| 4,104,005 | 8/1978 | Poirier . |
| 4,160,970 | 7/1979 | Nicolson .................. 166/66 |
| 4,184,811 | 1/1980 | Schade . |
| 4,252,015 | 2/1981 | Harbon et al. ............. 73/302 |
| 4,257,751 | 3/1981 | Kofahl . |
| 4,295,801 | 10/1981 | Bennett . |
| 4,360,320 | 11/1982 | Ower ...................... 417/394 |
| 4,377,550 | 3/1983 | Tokarz .................... 73/304 R |

OTHER PUBLICATIONS

"Procedures and Equipment for Groundwater Monitoring"-Industrial & Environmental Analysts, Inc.

Primary Examiner—William F. Pate, III
Attorney, Agent, or Firm—Harness, Dickey & Pierce

[57] ABSTRACT

A fluid sampling apparatus is disclosed for withdrawing samples of groundwater or other fluids from a well or other monitoring site. The apparatus preferably includes pump means, conduit means and a wellhead assembly that are substantially permanently installed at such well or monitoring site and are thereby dedicated thereto in order to avoid or minimize cross-contamination of samples from site to site. The apparatus preferably also includes a removable and portable controller means adapted for easy and convenient transportation and connection to such dedicated fluid sampling components at various wells or monitoring sites.

26 Claims, 8 Drawing Figures

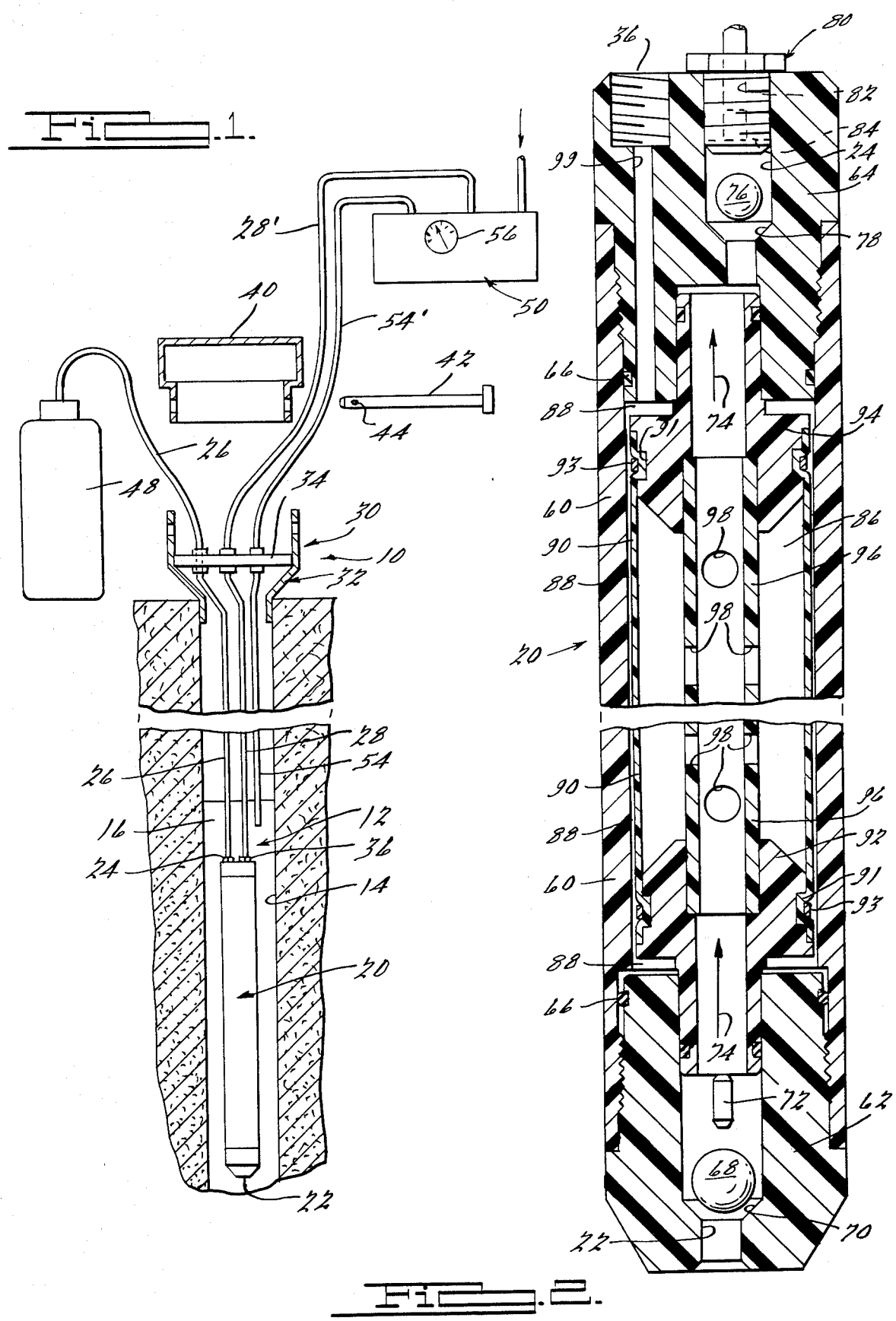

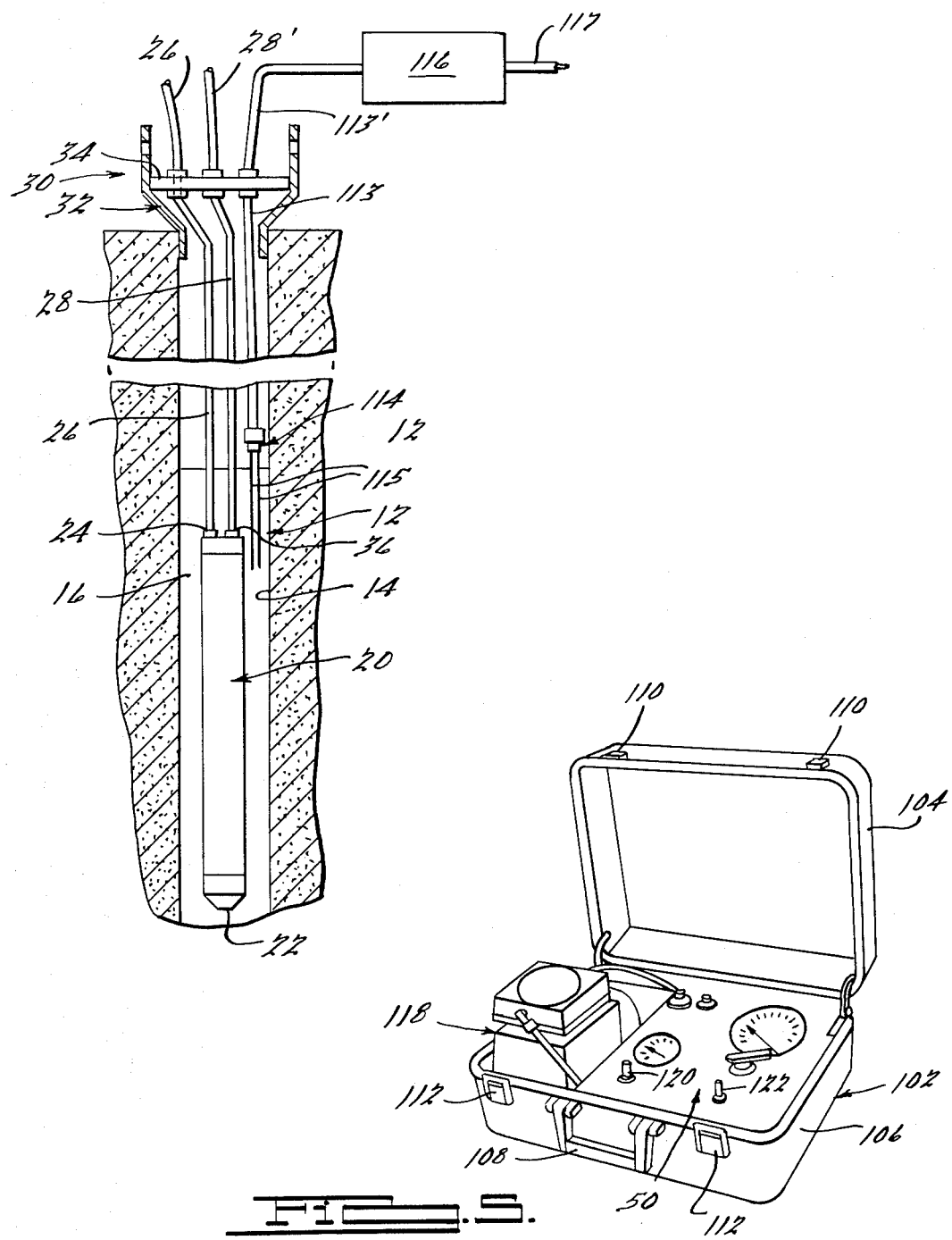

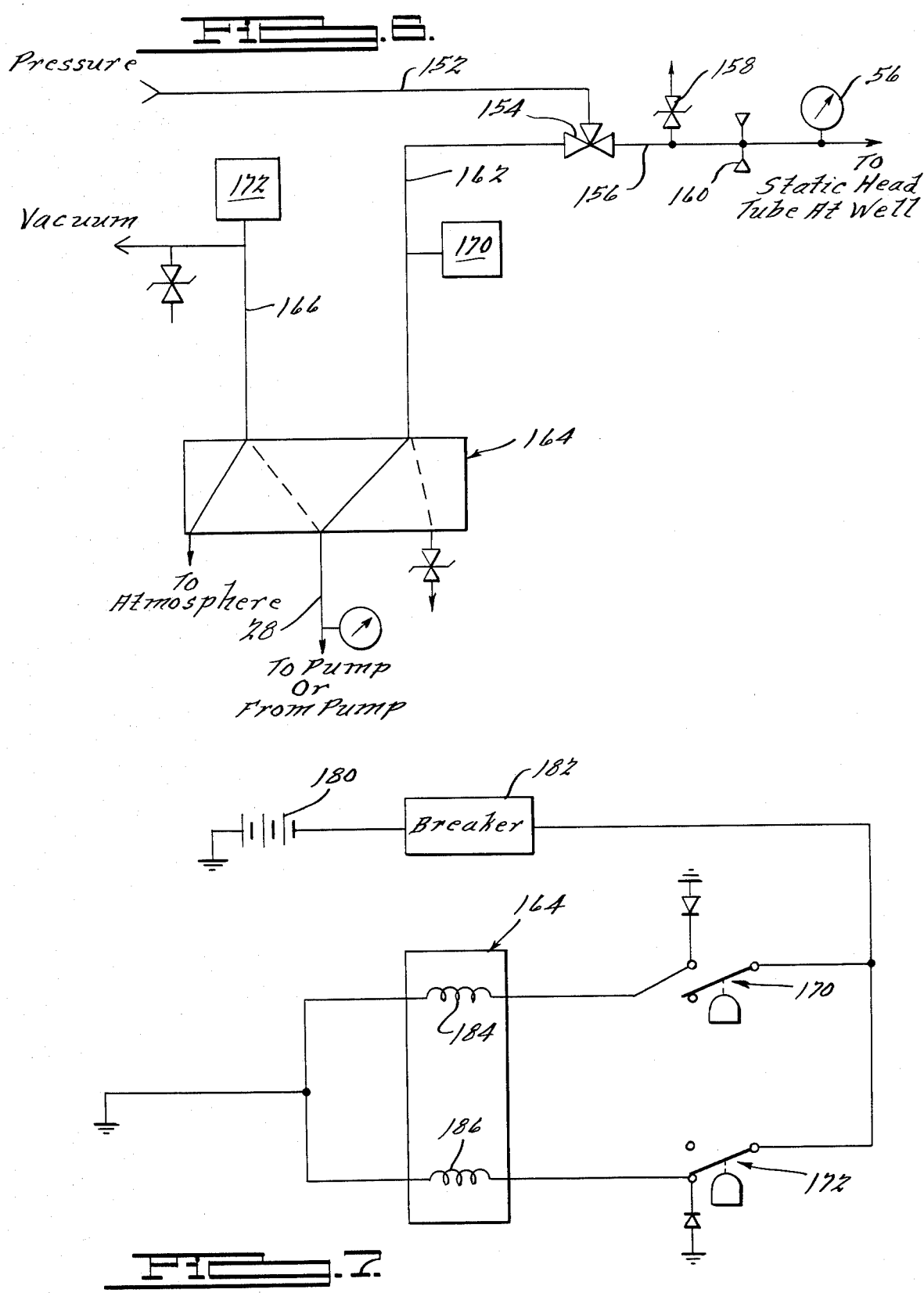

FLUID SAMPLING APPARATUS

BACKGROUND AND SUMMARY OF THE INVENTION

The invention relates generally to fluid pumping apparatus. More particularly, the preferred embodiment of the invention relates to apparatus for obtaining liquid samples from a well or the like.

Recent increases in public concern for the environment have resulted in various government-imposed environmental regulations. Among such regulations are requirements relating to the monitoring of groundwater quality. In response to these requirements, water quality analytic capabilities have been improved and water sampling equipment has been developed. Much of the previously-developed sampling equipment has not been effective, however, in obtaining consistent, non-contaminated water samples that are accurately representative of the water system from which the sample is taken.

The inadequacies of previous sampling equipment stem largely from such causes as cross-contamination between sampling sites, ineffective and inconsistent field cleaning methods, contamination due to equipment handling, and inconsistent well depth sampling. In addition to presenting sample quality problems, much of the previous equipment has been heavy and bulky and thus difficult to transport from one monitoring site to another. Finally, much of such previous equipment has proved to be complicated to operate, inordinately expensive, and impractical for sampling at remote locations where site access is severely limited.

In accordance with the present invention, a fluid sampling apparatus is provided for use in obtaining accurate samples of groundwater or other fluids. In the preferred embodiment, the pump is dedicated to a particular monitoring well or other sampling site in order to substantially avoid cross-contamination of samples from site-to-site and is constructed from lightweight, non-contaminating materials.

The preferred sampling pump is a submersible, fluid-actuated pump wherein the actuating fluid is preferably a gas. A flexible bladder member separates and isolates the interior of the pump into two chambers; a first chamber that contains the sample fluid and is in communication with both the pump inlet and outlet, and a second chamber that surrounds the first chamber, with the bladder disposed therebetween, and that is connected to a source of the actuating gas. The sample fluid is conveyed through the pump by alternately pressurizing and venting or relieving the pressure in the second chamber to contract and relax the bladder member, thus alternately decreasing and increasing the volume of the first chamber. Sample fluid is drawn into the first chamber during such increases in volume under the influence of the natural hydrostatic head of the groundwater and is discharged through the pump outlet during such decreases in volume, thereby conveying the sample fluid through the pump. The components of the pump are preferably composed of low-cost, lightweight synthetic materials that are non-corrosive and do not otherwise affect the chemical composition of the sampled fluid.

The sampling pump is preferably dedicated to, and thus remains in, a particular sampling site or well, which is substantially isolated from the above-ground surroundings by a wellhead assembly in order to reduce potential contamination during sampling. A portable controller apparatus is provided with quick connect-disconnect means and includes means for alternately pressurizing and de-pressurizing the actuating fluid. The fluid sampling apparatus may also optionally include means for measuring the standing level of the fluid in the well.

Additional advantages and features of the present invention will become apparent from the following description and the appended claims taken in conjunction with the accompanying drawings.

BRIEF DESCRIPTION OF THE DRAWINGS

FIG. 1 is a partially-exploded, longitudinal sectional view of a fluid sampling system according to the present invention.

FIG. 2 is an enlarged longitudinal cross-sectional view of the fluid sampling pump of FIG. 1.

FIG. 4 is a schematic representation of an optional apparatus for measuring the static head of the groundwater of the monitoring well of FIG. 1.

FIG. 5 is an overall perspective view of the controller apparatus of FIG. 1, shown housed in a portable carrying case.

FIG. 6 is a schematic representation of the fluid-actuating system of an alternate controller apparatus.

FIG. 7 is a schematic representation of the electrical system of the alternate controller apparatus of FIG. 6.

DETAILED DESCRIPTION OF THE PREFERRED EMBODIMENTS

Figure 3:
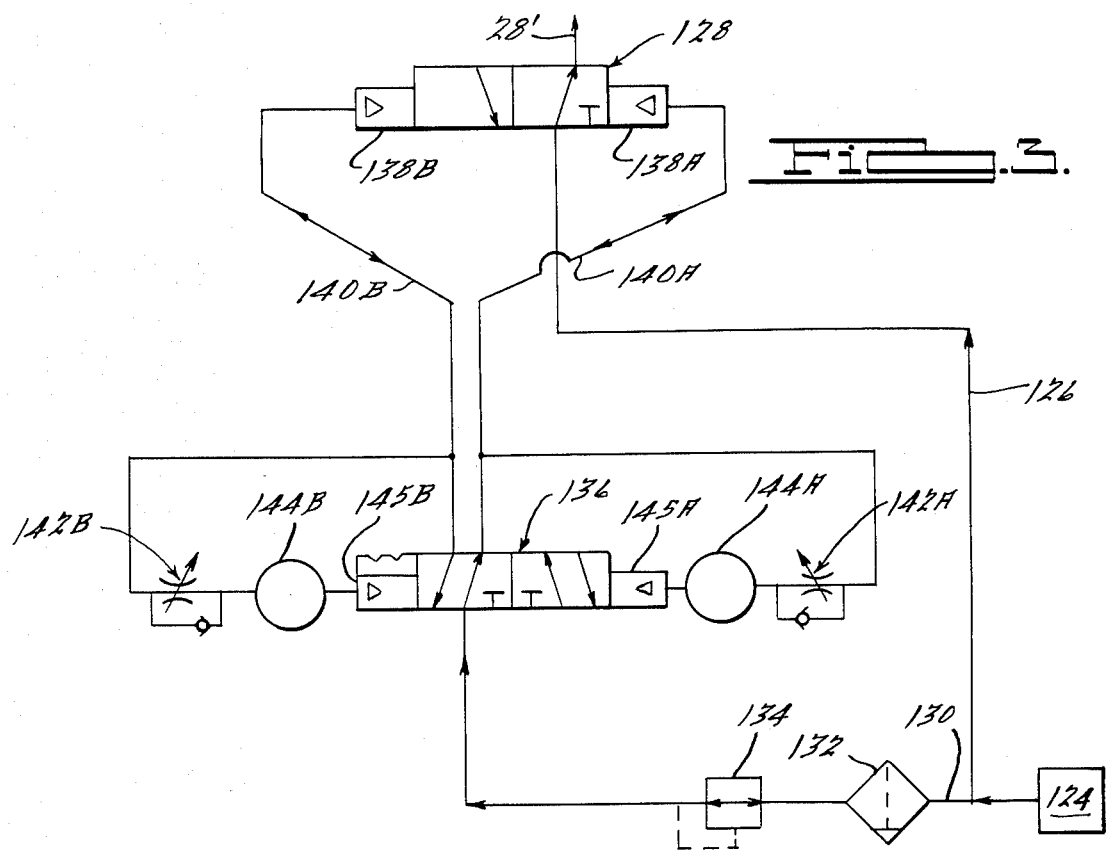
FIG. 3 is a schematic representation of the preferred controller apparatus of FIG. 1.

For purposes of illustration, FIGS. 1 through 7 of the drawings depict exemplary embodiments of a fluid sampling apparatus according to the present invention as installed in a monitoring well for withdrawing samples of groundwater. One skilled in the art will readily recognize from the following discussion that the principles of the invention are equally applicable to fluid sampling apparatus other than that shown in the drawings as well as to other fluid pumping apparatus.

In FIG. 1, an exemplary fluid sampling apparatus according to the present invention is indicated generally by reference numeral 10 and is shown for purposes of illustration as installed in a monitoring well 12, which preferably includes a well casing 14. A fluid sampling pump 20 is disposed within the well casing 14 of the monitoring well 12 and is submerged beneath the water level of the groundwater 16 to a suitable depth for obtaining accurate and representative groundwater samples.

As is explained in further detail below, the preferred fluid sampling pump 20 is a fluid-actuated pump, wherein the actuating fluid is preferably a gas such as air, for example, and includes an inlet port 22 and an outlet port 24. A wellhead assembly 30 is secured to the well casing 14 and includes a wellhead body portion 32 having a generally horizontal support plate 34 therein. The body portion 32 substantially isolates the interior of the well 12 from the above-ground surrounding environment in order to avoid or at least minimize contamination of the interior of the well which would result from contact between the groundwater 16 and the air or other elements. The wellhead assembly 30 also includes a groundwater conduit 26 sealingly connected at one end to the pump inlet 22 and passing through plate 34 to provide direct sample delivery to a sample collection vessel 48. A gas conduit 28 is connected at one end to a gas connection 36 on the pump 20 and at the other end to the support plate 34. Because the pump is preferably of a lightweight construction, the conduits may also be used to retain the pump in its submerged position in the well.

A controller apparatus 50, which is described in further detail below, is selectively and removably connected to the wellhead assembly 30 by means of external gas conduit 28'. The preferred controller apparatus 50 is a portable, lightweight unit and includes a source of an actuating gas and means for alternately positively pressurizing and venting or relieving the pressure of the actuating gas in order to operate the fluid sampling pump 20, as is explained below.

In order to further isolate the interior of the well 12 from above-ground contamination, the wellhead assembly 30 preferably includes a closure member 40 adapted to be secured to the body portion 32 by a locking pin 42 insertible through corresponding aligned apertures in the body portion 32 and in the closure member 40. The locking pin 42 preferably includes an aperture 44 at one end, through which a padlock of other suitable locking means may be inserted in order to substantially prevent unauthorized access to the interior portions of the wellhead assembly.

The wellhead assembly 30 may also optionally include a static head or measuring fluid conduit 54 having an open end extending beneath the surface of the groundwater 16 and an opposite end connected to the support plate 34. The controller apparatus 50 is connectable to the static head conduit 54 by means of an external static head or measuring fluid conduit 54' and includes means for supplying a measuring fluid to the static conduit 54. Such measuring fluid, which may be air, for example, is supplied at a pressure sufficient to force the groundwater out of the open end of the static head conduit 54. The pressure necessary to expel the groundwater from the open end of the static head conduit may be measured by a pressure measuring device, schematically represented by reference numeral 56, in order to determine the standing level of groundwater in the well 12. The standing level of the groundwater 16 is determined for purposes such as detecting changes in quantities of subterranian groundwater or for determining the volume of groundwater in the monitoring well so that the well may be purged of approximately three to five times the standing volume of groundwater in the well before the sample is taken.

Referring to FIG. 2, the fluid sampling pump 20 includes a generally hollow cylindrical pump body 60 having an inlet cap 62 and an outlet cap 64 preferably threadably attached to its opposite ends. The inlet and outlet caps 62 and 64, respectively, are sealed to the pump body 60 by means of O-rings 66 or other suitable sealing means known to those skilled in the art. The inlet cap 62 includes the inlet port 22 and check valve means for preventing backflow of groundwater or other fluids through the inlet port 22 from the interior of the pump. Such check valve means includes a ball 68 trapped between a ball seat 70 and a retainer member 72. Preferably, the retainer member 72 is a relatively thin and flat insert frictionally held in place within the enlarged portion of the inlet port 22. Thus, when groundwater is flowing properly through the pump in the direction indicated by flow arrows 74, the groundwater may flow around the ball 68 and the retainer member 72 into the interior of the pump. Backflow in a direction opposite that indicated by flow arrows 74 is substantially prevented by sealing engagement of the ball 68 with its ball seat 70. Similarly, the outlet cap 64 includes check valve means comprising ball 76 trapped between ball seat 78 and outlet fitting 80. Thus, flow through the pump in the direction indicated by flow arrows 74 is allowed to pass around the ball 76 and through the slot 84 and bore 82 of the outlet fitting 80. Back flow is substantially prevented, however, by sealing engagement of the ball 76 with its ball seat 78.

The interior of the pump body 60 is divided and isolated into two chambers by a generally cylindrical flexible bladder 90. The bladder 90 defines a groundwater chamber 86 in its interior and defines an annular gas chamber 88 between the bladder exterior and the interior wall surface of the pump body 60. The bladder 90 is sealingly connected to the spool pieces 92 and 94 at its opposite ends by means of rings 93 which are swaged or otherwise deformed to sealingly force the bladder material into the grooves 91 on the spool pieces 92 and 94. The rings 93 may be composed of a soft ductile metal or other readily deformable materials known to those skilled in the art. A connecting tube 96 in the groundwater chamber 86 extends between the spool pieces 92 and 94 and includes a number of apertures 98 spaced at various locations along its longitudinal length in order to allow the free flow of groundwater fluid between the interior of the connecting tube and the remainder of the groundwater chamber 86.

Referring to FIGS. 1 and 2, the preferred fluid sampling pump 20 is actuated by means of an actuating gas supplied to the gas chamber 88 which is alternately subjected to positive and negative or reduced pressures. The alternate pressurizing and depressurizing of the actuating gas in the gas chamber 88 causes the bladder 90 to alternately contract and relax, thus alternately decreasing and increasing the volume of the groundwater chamber 86. During such increases in volume, groundwater is drawn from the well 12 into the groundwater chamber 86 through the inlet port 22 in the inlet cap 62. During such decreases in such volume, the groundwater is forced out of the groundwater chamber 86 through the outlet port 24 in the outlet cap 64 and is passed through the groundwater conduit 26 to be collected in the sample collection vessel 48. The check valve means in each of the inlet and outlet caps 62 and 64, respectively, prevents the water from being discharged through the inlet port or drawn in through the outlet port. The capacity of the pump 20 may be changed by increasing the length of the pump body 60, and correspondingly increasing the length of the bladder 90 and the connecting tube 96, thereby changing the amount of water drawn in and forced out during the alternate contractions and relaxations of the flexible bladder 90.

It should be noted that except for the swaged rings 93, which do not contact the groundwater, the various components of the pump 20 are preferably composed of relatively lightweight and low-cost synthetic materials that will not be corroded when exposed to the groundwater 16 and will not otherwise affect the composition of the groundwater flowing through the pump. Examples of such materials include rigid polyvinyl chloride (PVC) or virgin grade tetrafluoroethylene (TFE) teflon. The flexible bladder is preferably composed of a flexible synthetic material which also will not corrode or affect the composition of groundwater flowing therethrough, such as flexible polyvinyl chloride, TFE, or VITON, for example. VITON is a trademark owned of E.I. Du Pont de Nemours & Company for its fluoroelastomer materials. One skilled in the art will readily recognize, however, that the various components of the fluid sampling apparatus may be composed of other suitable non-corrosive materials.

The preferred controller apparatus 50 generally includes the external gas conduit 28' and means for supplying an actuating gas to the gas chamber 88 of the pump 20 and for alternately pressurizing and venting, or relieving, the pressure of the actuating gas, as described above, in order to actuate the fluid sampling pump. The various physical components of the preferred controller apparatus 50 are well-known to those skilled in the art and thus are described in FIGS. 3 and 3A only schematically in terms of their functions.

As is represented schematically in FIG. 3, a pressurized actuating gas, such as air, for example, is supplied from an actuating gas source 124, such as a gas compressor, pressurized gas containers, or even a hand-operated pump, for example, through a gas supply line 126. The pressurization and vent cycles for the sampling pump are controlled by the action of three-way supply valve 128, which is in fluid communication with the gas source through the supply line 126. In its first valving mode, which is shown in FIG. 3, the three-way supply valve 128 connects the compressed gas source 124 to the gas conduit 28' and the sampling pump in order to contract the flexible bladder 90 and expel groundwater from the pump. In its second valving mode, supply valve 128 vents the gas conduit 28' to the open atmosphere thereby allowing groundwater to flow into the pump under the influence of its natural hydrostatic head. The supply valve 124 automatically alternates the pressurization and venting conditions by means of a pneumatic timing circuit.

Pressurized actuating gas from the gas source 124 is also conveyed through a conduit 130 to a filtration coalescence device 132 and then to a pressure regulator 134, which maintains gas pressure levels appropriate to proper functioning of the timing circuit components. The pressure-regulated gas flow is fed continuously to the control shuttle valve 136, which is a five-way type valve and which directs the pressure-regulated gas to one of the two pilot actuators 138A and 138B of the three-way supply valve 128 and to the corresponding pilot actuator 145A or 145B of the control shuttle valve 136.

When the control shuttle valve 136 is in its first valving mode shown in FIG. 3, the pilot actuator 138A on the supply valve 128 is pressure-actuated through conduit 140A, and the pilot actuator 138B is vented to atmosphere. When conduit 140A is pressurized, gas also flows at a controlled rate through an adjustable orifice in a flow control valve 142A and into a gas volume chamber 144A. When the gas pressure in the gas volume chamber 144A exceeds a predetermined level, the control shuttle valve 136 is driven by its pilot actuators 145A and 145B into its second valving mode. In such second mode, the gas in the gas volume chamber 144A and conduit 140A are bled through the adjustable orifice and a reversed check valve in the flow control valve 142A to be vented to atmosphere through the shuttle valve 136. Simultaneously, while the control shuttle valve is in such second mode, the previously vented conduit 140B is now pressurized, causing the pilot actuator 138B of the three-way valve 128 to be actuated. The pressure in conduit 140B also causes gas to flow through an adjustable orifice in flow control valve 142B and into a gas volume chamber 144B. When the gas pressure in the gas volume chamber 144B exceeds predetermined level, control shuttle valve 136 is actuated to again pressurize conduit 140A and to again vent conduit 140B to atmosphere. The gas volume chamber 144B is then vented to atmosphere through the flow control valve 142B. The pressurization of conduit 140A thus again begins the actuation of the pilot actuator 138A on the supply valve 128 and the resultant pressurization of gas volume chamber 144A to repeat the cycle.

The adjustment of the orifices in the flow control valves 142A and 142B control the rate at which the gas pressure rises in the gas volume chambers 144A and 144B. Thus, the conduits 140A and 140B are alternately pressurized and vented to atmosphere for time periods that are controlled by the gas flow rates through flow control valves 142A and 142B and by the size of gas volume chambers 144A and 144B. The gas pressure cycles in conduits 140A and 140B in turn actuate the pilot actuators 138A and 138B of the three-way supply valve 128, thus alternately pressurizing and venting the gas conduit 28 and the sampling pump.

Figure 3A:
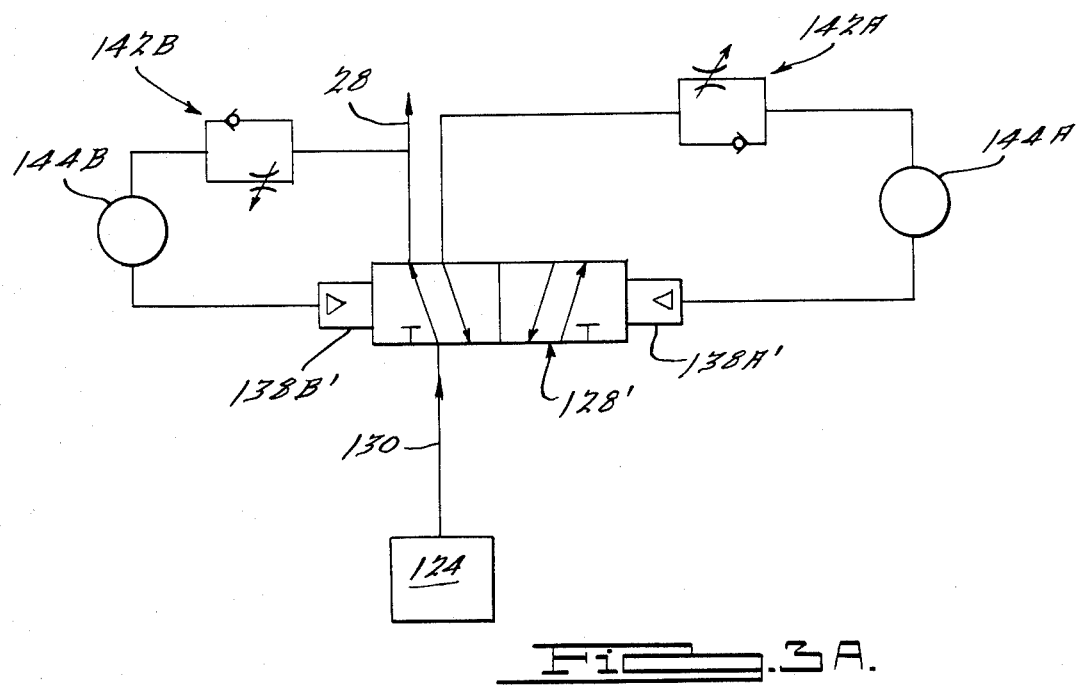
FIG. 3A is a schematic representation of an alternate variation on the controller apparatus of FIG. 3.

Alternate means may also be provided for automatically-cycling the three-way supply valve 128 between pressurization and venting cycles. For example, electronic timers may control an alternate solenoid-operated version of the valve 128, with one timer controlling the duration of each position or valving mode of the supply valve 128. An alternate pneumatic control circuit may also be provided for the supply valve, as represented schematically in FIG. 3A, with direct control of five-way valve 128' being accomplished by the pneumatic timing elements 142A, 144A, 142B and 144B described above, but without an intermediate control shuttle valve, such as the valve 136 of FIG. 3, and without the pressure regulator 134 or filter 132. One skilled in the art of pneumatic control devices would readily recognize that the selection between the systems of FIGS. 3 and 3A is based upon considerations of reliability, ease of operation, economy, and flexibility, given the particular application contemplated for the present invention.

FIG. 4 schematically illustrates an electronic version of the optional apparatus for measuring the hydrostatic head of the groundwater 16 in the monitoring well 12. It should be noted that such electronic version of the static head measuring apparatus may alternatively and optionally be employed in conjunction with either of the embodiments of the controller apparatus 50 shown in FIGS. 3 and 3A, or in conjunction with the controller apparatus schematically shown in FIGS. 6 and 7 and discussed below.

The optional static head measuring system schematically represented in FIG. 4 includes an electrical line 113 attached to the support plate 34 of the wellhead assembly 30 and extending into the monitoring well 12. The electrical line 113 is connected to a fluid level sensor 114, which preferably includes a pair of spaced apart electrical probe elements 115 extending into the groundwater 16. The probe elements 115, which are located closely adjacent one another relative to the distance from the probes to the casing 14 of the well, measure electrical quantities, such as conductivity or resistance, across the gap between the probe elements.

Since the groundwater and the air above the groundwater have distinct electrical conductivities and resistances, the electrical signal generated by the fluid level sensor changes as the level of the air-water interface correspondingly rises or falls along the probe elements 115. Such electrical signal therefore changes in accordance with any changes in the standing water level in the monitoring well.

The electrical line 113 is connectable, by way of a quick connect-disconnect fitting at the support plate 34, to an external electrical line 113' leading to an electronic processor 116. The processor 116, which preferably comprises a conventional microprocessor unit or other electronic circuitry known in the art, is adapted to receive and differentiate between the varying signals from the fluid level sensor 114 as the level of the air-water interface changes. The processor 116 is also adapted to generate an output signal, through an electrical output line 117 to indicating devices, such as gauges, indicator lights, or the like, on the controller apparatus 20 in order to detect and quantify such changes in the groundwater level in the well.

It should also be noted that alternatively only a single probe element 115 is necessary to measure the level of the groundwater in the well if another electrode is located on the pump body or some other location in the general vicinity of the fluid level sensor 114 and is electrically connected to the processor 116. In such a case the single probe would measure conductivity or resistance between itself and such an electrode and would generate a signal corresponding to the level of the groundwater.

FIG. 5 illustrates a preferred physical arrangement for the controller apparatus 50, including a carrying case 102 for housing and transporting the portable controller apparatus from one monitoring site to another. The carrying case 102 generally includes an upper portion 104 hingedly connected to a base portion 106, carrying handle means 108, and upper and lower latching means 110 and 112. The carrying case 102 is preferably composed of highly impact-resistant materials known to those skilled in the art for purposes of protecting the components of the controller apparatus. In the preferred embodiment shown for purposes of illustration in FIG. 5, the controller apparatus generally includes a gas compressor 118, a fitting 120 to which the external gas conduit 28' may be connected, a fitting 122 to which the external static head conduit 54' may be connected (or an electrical connector for the electronic head measuring system of FIG. 4), a power source for the gas compressor 118, and various controls and fluid gauges. The carrying case 102 is especially adapted for ease and convenience of transportation of the controller apparatus and related components to monitoring sites to which access is limited or difficult.

FIG. 6 schematically represents an alternate actuating gas system for an alternate controller apparatus 50. The various physical components of such alternate system are well-known to those skilled in the art and therefore will be described herein only schematically in terms of their functions. A positively or negatively pressurized actuating gas, such as air, for example, is supplied from an actuating gas source, such as a gas compressor, pressurized gas containers, or even a hand-operated pump, for example, through a gas supply line 152. If optional pneumatic apparatus for measuring the standing level of groundwater in the well 12 is to be included in the fluid sampling apparatus 10, the actuating gas may be supplied through the gas supply line 152 to a three-way valve 154. During groundwater standing level measurement, the three-way valve 154 is adjusted to divert the actuating gas through a conduit 156 for use as a measuring fluid to determine the standing groundwater level. The conduit 156 includes a safety valve 158, a pressure reducer 160 having a fixed or adjustable restrictive orifice and the pressure measuring device 56 referred to above, which preferably comprises a pressure gauge readable in inches of water. The actuating gas, which also functions as the measuring fluid, is conveyed through the static head conduits 54' and 54 at a pressure sufficient to force substantially all of the groundwater 16 out of the open end of the static head conduit 54. The pressure of the actuating gas/measuring fluid stabilizes as the groundwater is expelled from the open end of the static head conduit, and a static head pressure reading may then be taken on the pressure measuring device 56. The pressure measuring device 56 is previously calibrated so that its readings (in inches of water) may be compared with a previously-measured standing water level in the well 12 when the fluid sampling apparatus 10 was installed therein. Such stabilized pressure reading may thus be compared with the previous calibration level, thereby allowing determination of the standing groundwater level during subsequent measurements. It should be pointed out that the optional and alternate version of the static head measuring apparatus discussed herein in connection with the alternate controller apparatus of FIGS. 6 and 7 may also optionally and alternatively be employed in conjunction with the controller apparatus embodiments of FIGS. 3 and 3A, discussed above.

In order to pump a quantity of the groundwater 16 from the well 12, the three-way valve 154 is adjusted to divert the actuating gas from the gas supply line 152 to a shuttle valve 164 through a connecting line 162. A similar connecting line 166 interconnects the supply valve 164 with a vacuum or negative pressure source. The pressure connecting line 162 and the vacuum connecting line 166 include a pressure switch 170 and a vacuum switch 172, respectively, for actuating the shuttle valve 164 as described below.

When the supply valve 164 is in the valving mode or position illustrated by solid lines in FIG. 6, positively pressurized actuating gas is admitted to the gas chamber of the fluid sampling pump through the gas conduits 28' and 28 as shown in FIG. 1. Such positively pressurized actuating gas causes the pump bladder to contract in order to expel groundwater from the pump as described above. When the pressure switch 170 senses a predetermined positive pressure value in the pressure connecting line 162, it automatically causes the supply valve to switch to the valving mode or position indicated by broken lines in FIG. 6 in order to connect the gas chamber of the fluid sampling pump to the vacuum connecting line 166. The gas chamber of the fluid sampling pump is then subjected to a negative pressure in order to cause the flexible bladder to expand or relax to draw groundwater into the pump through the inlet port 22. Such expansion or relaxation continues until the vacuum switch 172 senses a negative pressure in the vacuum connecting line 166 of a predetermined negative pressure value. At such time the vacuum switch 172 causes the supply valve 164 to revert back to its valving mode shown in solid lines in FIG. 6, thereby reconnecting the gas chamber of the fluid sampling pump to the source of pressurized actuating gas by way of the pressure connecting line 162. Thus, as is described above, the gas chamber of the fluid sampling pump is alternately subjected to positive and negative actuating gas pressures thereby causing the flexible bladder to alternately contract and relax in order to cause the groundwater 16 to flow through the pump. Such alternate pressurizing and depressurizing of the gas chamber of the fluid sampling pump continues until the above-discussed purging of the well and withdrawal of a groundwater sample is complete.

FIG. 7 schematically represents an electronic schematic of a control system for use in conjunction with the actuating gas system shown schematically in FIG. 6. Preferably, a portable power source 180 and a circuit breaker 182 are connected to parallel switching circuits, one of such circuits including the pressure switch 170 and its associated electric actuator device 184 and the other of such circuits including the vacuum switch 172 and its associated electric actuator device 186. Thus, when the vacuum switch 172 senses a negative gas actuating fluid pressure equal to the above-mentioned predetermined value, the switch is closed to energize the electric actuator device 186 which causes the supply valve 164 to connect the fluid sampling pump to the pressurized actuating gas source as discussed above in connection with FIG. 6. Alternatively, when the pressure switch 170 senses an actuating gas pressure at the above-mentioned predetermined positive pressure value, the pressure switch closes to energize the electric actuator device 184 which causes the supply valve 164 to disconnect the source of pressurized actuating gas and connect the vacuum source to the fluid sampling pump as described above.

The foregoing discussion discloses and describes merely exemplary embodiments of the present invention. One skilled in the art will readily recognize from such discussion that various changes, modifications and variations may be made therein without departing from the spirit and scope of the invention as defined in the following claims.

What is claimed is:

1. A groundwater sampling apparatus for withdrawing groundwater samples from a groundwater monitoring well, said apparatus having dedicatable inground components to prevent the apparatus from contaminating another well, said apparatus comprising:

a gas-actuated pump adapted to be submerged in the groundwater within said well for pumping a portion of said groundwater therefrom, said pump being permanently dedicatable to said well and having a pump body portion including a gas chamber, a groundwater chamber having an inlet and an outlet, and a flexible bladder for isolating said gas chamber from said groundwater chamber, said groundwater chamber being in communication with said groundwater in said well through said inlet when said pump is submerged therein;

a wellhead assembly permanently dedicatable to said well and including a wellhead body portion adapted to be secured to said well to isolate the interior of said well from the above-ground surroundings, said wellhead assembly further including a gas conduit having one end sealingly connected to said gas chamber and an opposite end fixedly and sealingly connected to said wellhead body portion, a substantially continuous groundwater conduit having one end sealingly connected to said outlet of said groundwater chamber, said groundwater conduit substantially uninterruptedly passing through said wellhead assembly to an opposite end in communication with the above-ground surroundings for collecting a sample quantity of said groundwater from said well prior to substantial contact with the above-ground air; and controller apparatus including means selectively connectable to, and disconnectable from, said wellhead assembly in fluid communication with said gas conduit for supplying an actuating gas to said gas chamber of said pump and for alternately pressurizing and relieving the pressure of said actuating gas in said gas chamber in order to cause said bladder to alternately contract and relax and actuate said pump, said pump relying substantially upon the natural hydraulic head of said well to urge groundwater into said groundwater chamber upon relaxation of said bladder, said controller apparatus including a source of pressurized actuating gas, control valve means for connecting said pressurized gas source to said gas conduit and disconnecting said pressurized gas source therefrom in response to predetermined actuating gas pressure levels in said gas chamber, said controller apparatus being portable and transportable so as to be selectively connectable to, and disconnectable from, the gas conduit of said monitoring well or to the gas conduit of correlative dedicated inground components in similar monitoring wells.

2. A groundwater sampling apparatus according to claim 1, wherein said pump includes first check valve means for preventing backflow of said groundwater from said groundwater conduit into said pump through said outlet, and second check valve means for preventing backflow of said groundwater from said groundwater chamber out of said pump through said inlet.

3. A groundwater sampling apparatus according to claim 1, wherein said wellhead assembly further comprises a closure member adapted to be removably and lockably secured to said body portion when said controller apparatus is disconnected in order to substantially isolate said gas, groundwater and static heat conduits from said above-ground surroundings and to substantially prevent unauthorized access thereto.

4. A groundwater sampling apparatus according to claim 1, wherein said wellhead assembly further comprises a static head conduit having an open end extending below the surface of said groundwater in said well and a second end connected to said body portion, said controller apparatus further including means selectively connectable to, and disconnectible form, said static head conduit for supplying a measuring fluid thereto at a pressure sufficient to force substantially all of said groundwater out of said open end of said static head conduit, said controller apparatus further including means for measuring the pressure of said measuring fluid in order to determine the level of said groundwater in said well.

5. A groundwater sampling apparatus according to claim 1, wherein said wellhead assembly further comprises sensing means extending below the surface of said groundwater in said well, said sensing means being adapted for generating a distinct signal corresponding to the level of said groundwater in said well, and processing means for receiving said signal and for providing an indication corresponding to said groundwater level.

6. A liquid sampling apparatus according to claim 5, wherein said sensing means includes a pair of elongated probes protruding generally downwardly into said groundwater in said well, said probes being separated but located closely adjacent one another relative to the distance from said probes to the lateral periphery of said well.

7. A groundwater sampling apparatus according to claim 1, wherein said controller apparatus includes:
   a source of said actuating gas under pressure;
   supply valve means connected to said source of said gas and being actuable into a pressurizing mode to provide gas communication between said source of said gas and said gas conduit and actuable into a relief mode to provide gas communication between said gas conduit and a region having a pressure lower than that of said source; and
   pneumatic timing control means for alternately actuating said supply valve means into said pressurizing mode for a first predetermined time period and actuating said supply means into said relief mode for a second predetermined time period, thereby causing the pressure of said gas in said chamber to be alternately raised and lowered.

8. A groundwater sampling apparatus according to claim 7, wherein said supply valve means is pneumatically actuable into said pressurizing and relief modes, said pneumatic timing control means including a control valve means also connected to said source of said gas andd being pneumatically actuable into a first mode wherein said control valve means provides gas communication between said source of said gas and said supply valve means for pneumatically actuating said supply valve means into said pressurizing mode, said control valve further being pneumatically actuable into a second mode wherein said control valve means provides gas communication between said source of said gas and said supply valve means for pneumatically actuating said supply valve means into said relief mode, said pneumatic timing control means being adapted to actuate said control valve means into said first mode in response to a first predetermined gas pressure level between said control valve means and said supply valve means and further being adapted to actuate said control valve means into said second mode in response to a second predetermined gas pressure level between said control valve means and said supply valve means.

9. A groundwater sampling apparatus according to claim 8, wherein said gas in said chamber is vented to the atmosphere when said supply valve means is actuated into said relief mode.

10. A groundwater sampling apparatus according to claim 7, wherein said timing control means includes means for actuating said supply valve means into said pressurized and relief mode in response to predetermined pressure levels of said gas flowing through said supply valve means.

11. The improvement according to claim 1, wherein substantial portions of said pump, including said pump body portion and said flexible bladder, are composed of a polymeric material.

12. A groundwater sampling apparatus for withdrawing groundwater samples from a groundwater monitoring well, said apparatus having dedicatable inground components to prevent the apparatus from contaminating another well, a gas-actuated water sampling pump having a gas chamber for receiving a gas therein, a controller system for alternately pressurizing said gas in said gas chamber and relieving the pressure of said gas in said gas chamber, the improvement wherein said water sampling pump is substantially installed in, and dedicated to, said groundwater monitoring well, and said controller system including:
   a source of said gas under pressure;
   supply valve means connected to said source of said gas and being actuable into a pressurizing mode to provide gas communication between said source of said gas and said gas chamber and actuable into a relief mode to provide gas communication between said gas chamber and a region having a pressure lower than that of said source;
   pneumatic timing control means for alternately actuating said supply valve means into said pressurizing mode for a first predetermined time period and actuating said supply means into said relief mode for a second predetermined time period, thereby causing the pressure of said gas in said chamber to be alternately raised and lowered; and
   said supply valve means being pneumatically actuable into said pressurizing and relief modes, said pneumatic timing control means including a control valve means also connected to said source of said gas and being pneumatically actuable into a first mode wherein said control valve means provides gas communication between said source of said gas and said supply valve means for pneumatically actuating said supply valve means into said pressurizing mode, said control valve means further being pneumatically actuable into a second mode wherein said control valve means provides gas communication between said source of said gas and said supply valve means for pneumatically actuating said supply valve means into said relief mode, said pneumatic timing control means being adapted to actuate said control valve means into said first mode in response to a first predetermined gas pressure level between said control valve means and said supply valve means, and said pneumatic timing control means further being adapted to actuate said control valve means into said second mode in response to a second predetermined gas pressure level between said control valve means and said supply valve means,
   said controller system being portable so as to be selectively connectable to and disconnectable from said sampling pump in said monitoring well or to a correlative dedicated inground sampling pump in similar monitoring wells.

13. The improvement according to claim 12, wherein said gas in said gas chamber is vented to the atmosphere when said supply valve means is actuated into said relief mode.

14. The improvement according to claim 12, wherein said timing control means includes means for actuating said supply valve means into said pressurized and relief modes in response to predetermined pressure levels of said gas flowing through said supply valve means.

15. A groundwater sampling apparatus for withdrawing groundwater samples from a groundwater well, said apparatus having dedicatable inground components to prevent the apparatus from contaminating other monitoring wells, said apparatus having a gas-actuated water sampling pump for the groundwater monitoring well, said water sampling pump having a gas chamber for receiving a gas therein, a controller system for alternately pressurizing said gas in said gas chamber and relieving the pressure of said gas in said gas chamber, the improvement wherein said water sampling pump is substantially installed in, and dedicated to, said groundwater monitoring well, said controller system being portable and being selectively connectable to, and disconnectable from said water sampling pumps or to correlative dedicated inground sampling pumps in similar groundwater monitoring wells, said controller system including:

a source of said gas under pressure;
   supply valve means connected to said source of said gas and including first electric solenoid actuating means energizable for actuating said supply valve means into a pressurizing mode to provide gas communication between said source of said gas and said gas chamber, said supply valve means further including second electric solenoid actuating means energizable for actuating said supply valve means into a relief mode to provide gas communication between said gas chamber and a region having a pressure lower than that of said source; and
   electric timing control means for alternately energizing said first and second electric solenoid actuating means in order to alternately actuate said supply valve means into said pressurizing mode for a first predetermined time period and into said relief mode for a second predetermined time period, thereby causing the pressure of said gas in said chamber to be alternately raised and lowered.

16. The improvement according to claim 15, wherein said gas in said gas chamber is vented to the atmosphere when said supply valve means is actuated into said relief mode.

17. A groundwater sampling apparatus according to claim 15, wherein said wellhead assembly further comprises a static head conduit having an open end extending below the surface of said groundwater in said well and a second end fixedly and sealingly connected to said wellhead assembly, said controller apparatus further including means selectively connectable to, and disconnectable from, said wellhead assembly in fluid communication with said static head conduit for supplying a measuring fluid thereto at a pressure sufficient to force substantially all of said groundwater out of said open end of said static head conduit, said controller apparatus further including means for measuring the pressure of said measuring fluid in order to determine the level of said groundwater in said well.

18. A groundwater sampling apparatus according to claim 16, wherein said wellhead assembly further comprises a closure member removably and lockably securable to said wellhead assembly when said controller apparatus is disconnected in order to substantially isolate said gas, groundwater and static head conduits from said above-ground surroundings and to substantially prevent unauthorized access thereto.

19. A groundwater sampling apparatus for withdrawing groundwater samples from a groundwater monitoring well, said apparatus having dedicatable inground components to prevent the apparatus from contaminating similar groundwater monitoring wells, comprising:

a gas-actuated pump adapted to be submerged in the groundwater within said well for pumping a portion of said groundwater therefrom, said pump being substantially permanently installable in, and dedicatable to, said well and having a pump body portion including a gas chamber, a groundwater chamber having an inlet and an outlet, and a flexible bladder for isolating said gas chamber from said groundwater chamber, said groundwater chamber being in communication with said groundwater in said well through said inlet when said pump is submerged therein, substantial portions of said pump, including said pump body portion and said flexible bladder being composed of a polymeric material;
   a wellhead assembly substantially permanently installable on, and dedicatable to said well and including a wellhead body portion adapted to be secured to said well to isolate the interior of said well from the above-ground surroundings, said wellhead assembly further including a gas conduit having one end sealingly connected to said gas chamber and an opposite end fixedly and sealingly connected to said wellhead body portion, a groundwater conduit having one end sealingly connected to said outlet of said groundwater chamber and substantially uninterruptedly passing through said wellhead assembly to an opposite end in communication with the above-ground surroundings for collecting a sample quantity of said groundwater from said well; and
   controller apparatus including means selectively connectable to, and disconnectable from, said wellhead assembly in fluid communication with said gas conduit for supplying an actuating gas to said gas chamber of said pump and for alternately pressurizing and relieving the pressure of said actuating gas in said gas chamber in order to cause said bladder to alternately contract and relax to actuate said pump,
   valve means and said supply valve means, and said pneumatic timing control means further being adapted to actuate said control valve means into said second mode in response to a second predetermined gas pressure level between said control valve means and said supply valve means, said gas in said gas chamber being vented to the atmosphere when said supply valve means is actuated into said relief mode, and said timing control means including means for actuating said supply valve means into said pressurized and relief modes in response to predetermined pressure levels of said gas flowing through said supply valve means,
   said controller system being portable so as to be selectively connectable to and disconnectable from said sampling pump in said monitoring well or to a correlative dedicated inground sampling pump in similar monitoring wells.

20. A groundwater sampling apparatus according to claim 19, wherein said wellhead assembly further comprises a static head conduit having an open end extending below the surface of said groundwater in said well and a second end fixedly and sealingly connected to said wellhead assembly, said controller apparatus further including means selectively connectable to, and disconnectable from, said wellhead assembly in fluid communication with said static head conduit for supplying a measuring fluid thereto at a pressure sufficient to force substantially all of said groundwater out of said open end of said static head conduit, said controller apparatus further including means for measuring the pressure of said measuring fluid in order to determine the level of said groundwater in said well.

21. A groundwater sampling apparatus according to claim 20, wherein said wellhead assembly further comprises a closure member removably and lockably securable to said wellhead assembly when said controller apparatus is disconnected in order to substantially isolate said gas, groundwater and static head conduits from said above-ground surroundings and to substantially prevent unauthorized access thereto.

22. The improvement according to claim 21, wherein substantial portions of said pump, including said pump body portion and said flexible bladder, are composed of a polymeric material.

23. A groundwater sampling apparatus for withdrawing groundwater samples from a groundwater monitoring well, said apparatus having dedicatable inground components to prevent the apparatus from contaminating similar groundwater monitoring wells, comprising:

a gas-actuated pump adapted to be submerged in the groundwater within said well for pumping a portion of said groundwater therefrom, said pump being substantially permanently installable in, and dedicatable to, said well and having a pump body portion including a gas chamber, a groundwater chamber having an inlet and an outlet, and a flexible bladder for isolating said gas chamber from said groundwater chamber, said groundwater chamber being in communication with said groundwater in said well through said inlet when said pump is submerged therein, substantial portions of said pump, including said pump body portion and said flexible bladder being composed of a polymeric material;

a wellhead assembly substantially permanently installable on, and dedicatable to said well and including a wellhead body portion adapted to be secured to said well to isolate the interior of said well from the above-ground surroundings, said wellhead assembly further including a gas conduit having one end sealingly connected to said gas chamber and an opposite end fixedly and sealingly connected to said wellhead body portion, a groundwater conduit having one end sealingly connected to said outlet of said groundwater chamber and substantially uninterruptedly passing through said wellhead assembly to an opposite end in communication with the above-ground surroundings for collecting a sample quantity of said groundwater from said well; and controller apparatus including means selectively connectable to, and disconnectable from, said wellhead assembly in fluid communication with said gas conduit for supplying an actuating gas to said gas chamber of said pump and for alternately pressurizing and relieving the pressure of said actuating gas in said gas chamber in order to cause said bladder to alternately contract and relax to actuate said pump, said controller apparatus further including a source of said gas under pressure, supply valve means connected to said source of said gas and including first electric solenoid actuating means energizable for actuating said supply valve means into a pressurizing mode to provide gas communication between said source of said gas and said gas chamber, said supply valve means further including second electric solenoid actuating means energizable for actuating said supply valve means into a relief mode to provide gas communication between said gas chamber and a region having a pressure lower than that of said source, and electric timing control means for alternately energizing said first and second electric solenoid actuating means in order to alternately actuate said supply valve means into said pressurized mode for a first predetermined time period and into said relief mode for a second predetermined time period, thereby causing the pressure of said gas in said gas chamber to be alternately raised and lowered, said gas in said gas chamber being vented to the atmosphere when said supply valve means is actuated into said relief mode, said controller system being portable so as to be selectively connectable to and disconnectable from said sampling pump in said monitoring well or to a correlative dedicated inground sampling pump in similar monitoring wells.

24. A groundwater sampling apparatus according to claim 23, wherein said wellhead assembly further comprises a static head conduit having an open end extending below the surface of said groundwater in said well and a second end fixedly and sealingly connected to said wellhead assembly, said controller apparatus further including means selectively connectable to, and disconnectable from, said wellhead assembly in fluid communication with said static head conduit for supplying a measuring fluid thereto at a pressure sufficient to force substantially all of said groundwater out of said open end of said static head conduit, said controller apparatus further including means for measuring the pressure of said measuring fluid in order to determine the level of said groundwater in said well.

25. A groundwater sampling apparatus according to claim 24, wherein said wellhead assembly further comprises a closure member removably and lockably securable to said wellhead assembly when said controller apparatus is disconnected in order to substantially isolate said gas, groundwater and static head conduits from said above-ground surroundings and to substantially prevent unauthorized access thereto.

26. The improvement according to claim 25, wherein substantial portions of said pump, including said pump body portion and said flexible bladder, are composed of a polymeric material.

* * * * *

UNITED STATES PATENT AND TRADEMARK OFFICE
CERTIFICATE OF CORRECTION

PATENT NO. : 4,489,779

DATED : 12/25/84

INVENTOR(S) : William D. Dickinson et al

It is certified that error appears in the above-identified patent and that said Letters Patent is hereby corrected as shown below:

Col. 4, line 20, delete "swaged" and insert --swagged--

Col. 4, line 58, delete "swaged" and insert --swagged--

Col. 11, line 30, delete "andd" and insert --and--

Col. 12, line 61, following "groundwater" insert --monitoring--

Col. 14, line 34 before "valve" insert --said controller apparatus further including a source of said gas under pressure, supply valve means connected to said source of said gas and being actuable into a pressurizing mode to provide gas communication between said source of said gas and said gas chamber and actuable into a relief mode to provide gas communication between said gas chamber and a region having a pressure lower than that of said source, and pneumatic timing control means for alternately actuating said supply valve means into said pressurized mode for a first predetermined time period and actuating said supply means into said relief mode for a second predetermined time period, thereby causing the pressure of said gas in said gas chamber to be alternately raised and lowered, said supply valve means being pneumatically actuable into said pressurizing and relief modes, said pneumatic timing control means including a control valve means also connected to said source of said gas and being pneumatically actuable into a first mode wherein said control valve means provides gas communication between said source of said gas and said supply valve means for pneumatically actuating said supply valve means into said

UNITED STATES PATENT AND TRADEMARK OFFICE
CERTIFICATE OF CORRECTION

PATENT NO. : 4,489,779

DATED : 12/25/84

INVENTOR(S) : William D. Dickinson et al

It is certified that error appears in the above-identified patent and that said Letters Patent is hereby corrected as shown below:

pressurizing mode, said control valve means further being pneumatically actuable into a second mode wherein said control valve means provides gas communication between said source of said gas and said supply valve means for pneumatically actuating said supply valve means into said relief mode, said pneumatic timing control means being adapted to actuate said control valve means into said first mode in response to a first predetermined gas pressure level between said control--

Signed and Sealed this

Second Day of July 1985

[SEAL]

*Attest:*

DONALD J. QUIGG

*Attesting Officer*     *Acting Commissioner of Patents and Trademarks*